United States Patent [19]
Allotta

[11] Patent Number: 6,033,409
[45] Date of Patent: Mar. 7, 2000

[54] SURGICAL DRILL WITH BIT PENETRATION CONTROL AND BREAKTHROUGH DETECTION

[75] Inventor: Benedetto Allotta, Pontedera, Italy

[73] Assignee: Scuola Superiore Di Studi Universitari, Italy

[21] Appl. No.: 09/297,391

[22] PCT Filed: Oct. 31, 1997

[86] PCT No.: PCT/EP97/06020

§ 371 Date: Apr. 30, 1999

§ 102(e) Date: Apr. 30, 1999

[87] PCT Pub. No.: WO98/18390

PCT Pub. Date: May 7, 1998

[51] Int. Cl.[7] ........................................... A61B 17/16
[52] U.S. Cl. ............................................ 606/80; 606/170
[58] Field of Search .......................... 606/79, 80, 83, 606/170, 172, 180; 508/19, 132

[56] References Cited

U.S. PATENT DOCUMENTS 3,897,166  7/1975  Adams ........................................ 408/14

FOREIGN PATENT DOCUMENTS

0102412  3/1984  European Pat. Off. .
0343622  11/1989  European Pat. Off. .

Primary Examiner—Michael Buiz
Assistant Examiner—Daphna Shai
Attorney, Agent, or Firm—Simpson, Simpson & Snyder

[57] ABSTRACT

A surgical drill (1), comprising a rotating head (2) having a drill bit (3) suitable to bore a body (4) and support means (7) to which the head (2) is pivotally connected. An actuating unit (10) of the movement of the drill bit (3) with respect to the body to bore (4) is provided for, comprising a first support (11) comprising the head (2) and a second support (12), suitable for resting directly upon the body (4) and translating with respect to the first support (11) parallel to the drill bit (3). The movement between drill bit (3) and body (4) is caused by the relative movement between drill bit (3) and second support (12). Means (21) for the detection of the force acting on the drill bit and means for the control of the drill bit displacement in function of the drilling force are provided for. The drill, manually holdable, presents both a reference with respect to the patient body and allows a precise control of the drill bit displacement.

15 Claims, 7 Drawing Sheets

SURGICAL DRILL WITH BIT PENETRATION CONTROL AND BREAKTHROUGH DETECTION

DESCRIPTION

1. Field of the invention

The present invention generally relates to the field of apparatus for orthopaedic surgery and, more precisely, it relates to a surgical drill and actuating unit with drill bit penetration control and breakthrough detection.

2. Description of the prior art

It is at present felt by surgeons the need of a drill having sensors which can control the drill bit penetration while making a bore in a tissue, in particular a bone wall.

In fact, a surgical drill is often used for osteosynthesis operations and is guided manually by the surgeon, who carries out the drilling step according to his/her experience. For example, when transversally drilling a bone, the surgeon often has either to bore both the two cortical bone walls, making a substantially through hole, or has to bore only one wall, either passing through or not passing through the trabecular or medullar bone. However, it is difficult to carry out a correct drilling step without an automatic control of the drill bit displacement and of the drill bit piercing force and this depends totally on the surgeon's skill, who is also aware that to bore more than necessary could be useless and harmful for the patient.

Moreover, the drilling step has often to be carried out uncomfortably, according to the drilling direction with respect to the patient, and the more it is difficult and the more the risk of error rises. The surgeon, in any case, however skill, cannot reduce beyond certain limits the drill bit displacement error.

On the other hand, even if an industrial drill can be mounted on a fixed support having mechanically adjustable displacement means, this solution cannot be used in the case of a surgical drill, since the parts to be bored, differently from what occurs in the industrial field, cannot be fixed to reliable reference surfaces.

U.S. Pat. No. 3,897,166 describes a drill which can also be used in medical work such as bone drilling. The drill support comprises a pressure foot at its forward end to contact a work piece to be drilled. The support carries out the feed control of the pressure foot by means of a slide operated by the drive shaft of the drill. Therefore, pressure applied to the drill motor does not cause directly penetration of the work piece, such penetration being proportional to the speed of the drive shaft with respect to the pressure foot. Since the bit cannot advance freely, it cannot surge or jam when it breaks through the rear of the work piece.

However, U.S. Pat. No. 3,897,166 does not provide means for preventing the drill bit from breaking through a cortical wall of a bone, thus causing serious damages to the patient. In fact, the drill bit displacement is continuously fed unless the operator decides to stop the drive shaft rotation.

OBJECT OF THE INVENTION

It is, therefore, object of the present invention to provide a surgical drill which allows at the same time, even if handled manually:

to get a reference support on the patient and thus a more precise control of the drill bit penetration in the body to bore with respect to a drill of known art, the control of the drilling force and provides a stop of the drill bit when the breakthrough is incipient. In alternative, it is object of the invention to provide an actuating unit, which can be associated to an already existing surgical drill, that allows the control of the drill bit displacement and of the drilling force with respect to the body to bore as well as provides a stop of the drill bit when the breakthrough is incipient.

These and other objects are achieved by the surgical drill and by the actuating unit according to the invention, comprising a first support for a rotating head holding the drill bit, wherein means for preventing a wall of the body from being broken through by said drill bit are provided. The means for preventing comprise in combination:

a second support, suitable for resting directly upon the patient and translating with respect to the first support parallelly to the drill bit, means for detecting in the first support the force acting on the drill bit while drilling, and means for controlling the displacement of the first support with respect to the second support and responsive to the means of detection of the force, whereby both a reliable guide of the drill bit and an automatic stop of the displacement of the drill bit in case of breakthrough condition are provided.

BRIEF DESCRIPTION OF THE DRAWINGS

Further characteristics and advantages of the apparatus according to the present invention will become more apparent in the description which follows of some of its embodiments, given as an example and not limitative, with reference to the attached drawings in which.

DESCRIPTION OF PREFERRED EMBODIMENTS

Figure 1:
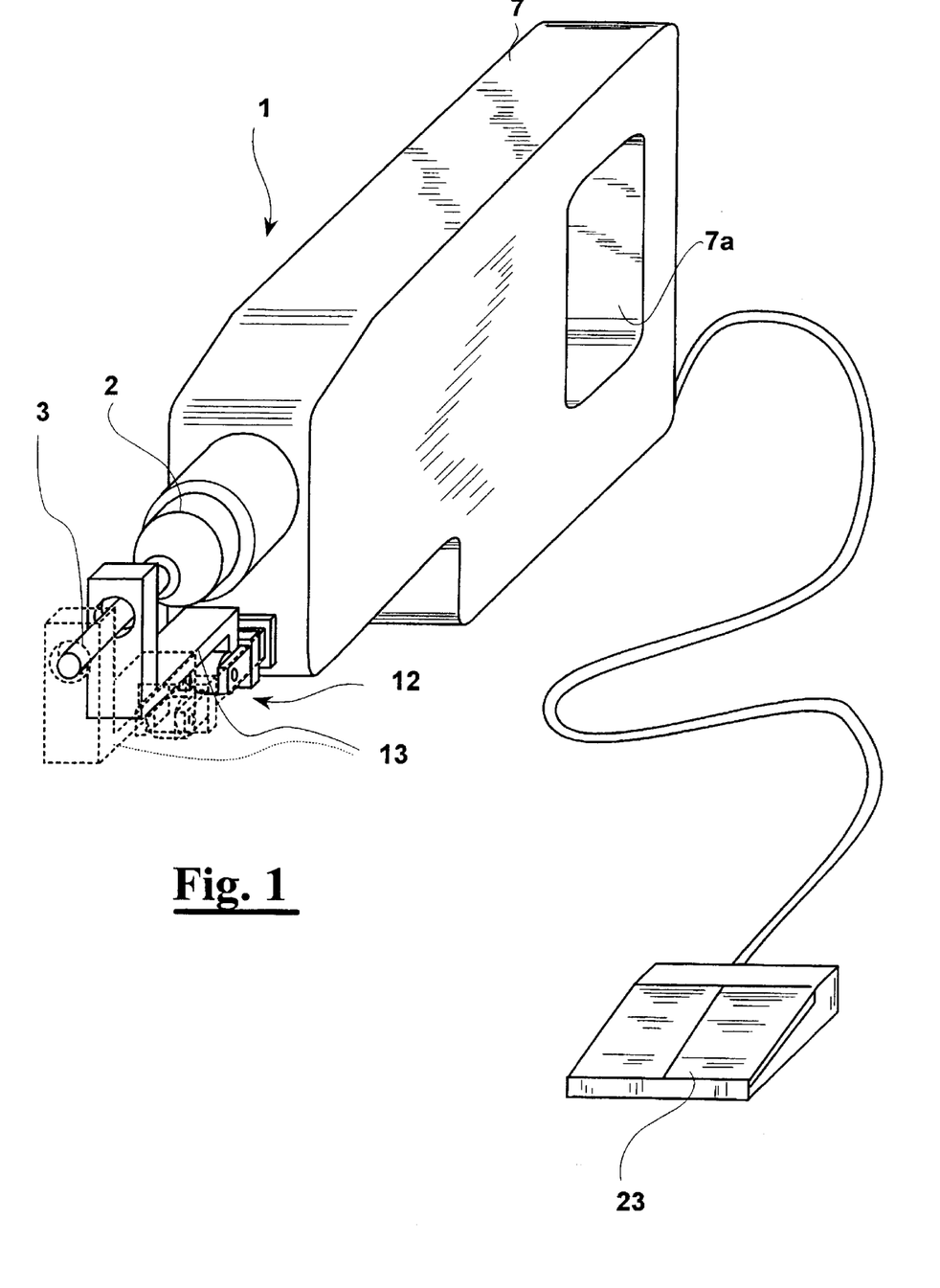
FIG. 1 shows a perspective view of a surgical drill according to the present invention.
Figure 2:
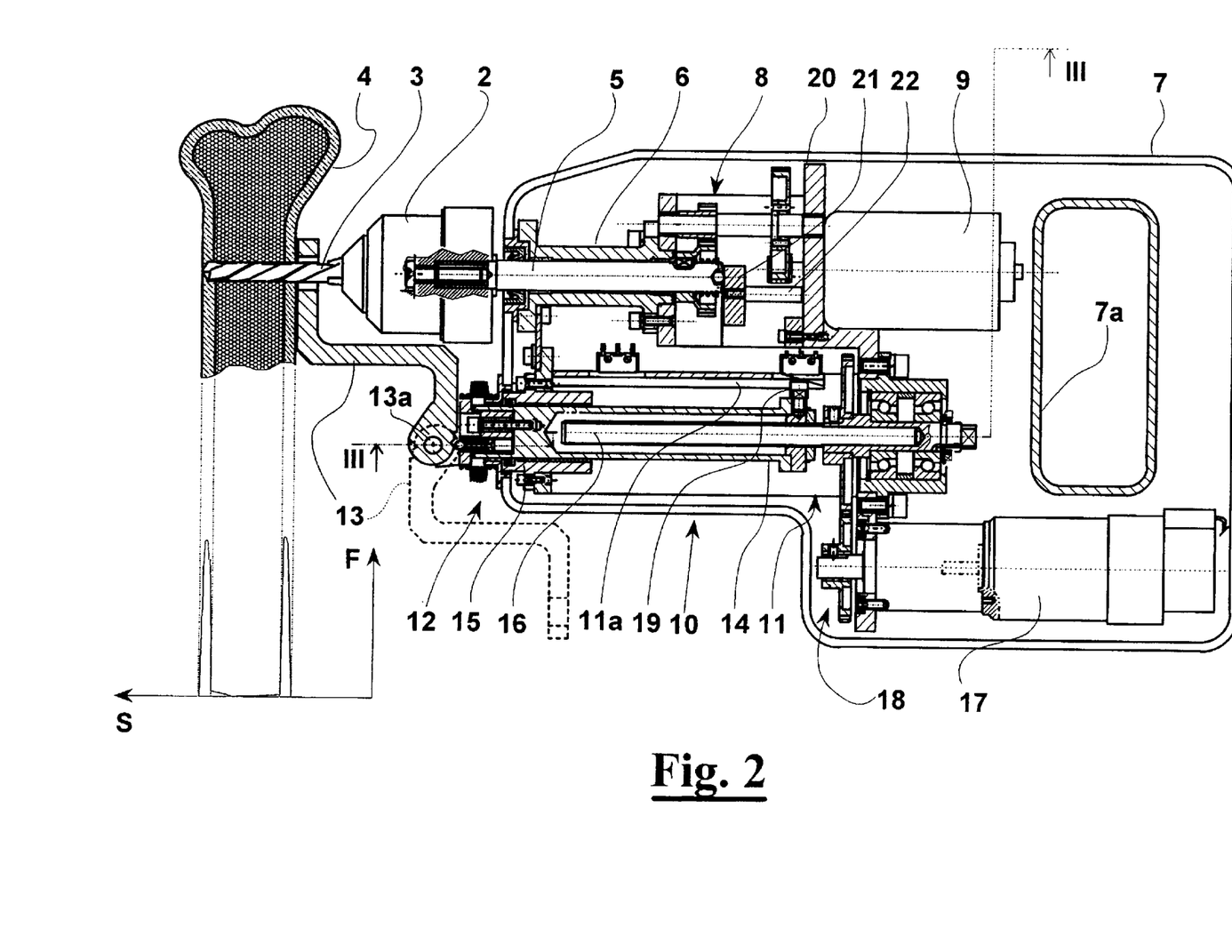
FIG. 2 is a cross sectional view by a longitudinal plane of the surgical drill of FIG. 1.
Figure 3:
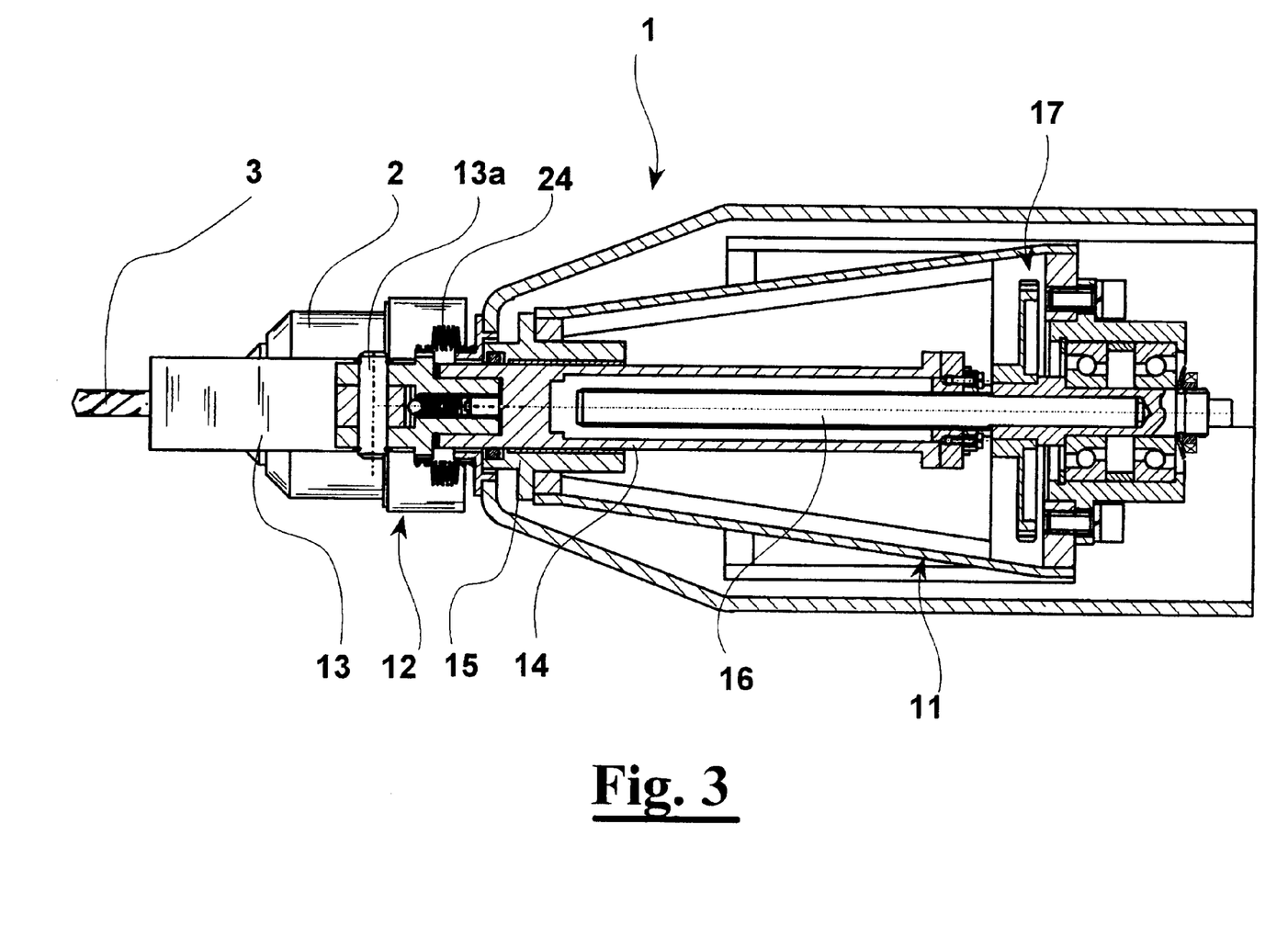
FIG. 3 shows a cross sectional view according to arrows III—III of the drill of FIG. 2.

With reference to FIGS. 1 to 3, a surgical drill 1 comprises a rotating head 2 having a drill bit 3 suitable to bore a body 4 (FIG. 2), such as a body bone, during a surgical operation of osteosynthesis. Head 2 (FIGS. 2 and 3) is pivotally connected by means of a shaft 5 to a housing 6 mounted in a casing 7 having a handgrip 7a to hold the drill 1. With housing 6 engages also a gearing 8 which rotates shaft 5 operated by a motor 9.

Always with reference to FIGS. 2 and 3, to casing 7 is connected also an actuating unit 10 suitable to guide drill bit 3 with respect to body 4. More precisely, actuating unit 10 comprises a first support 11, integral to housing 6, and a second support 12 capable of resting on body 4. Second support 12 comprises a rest element 13 and a nut screw element 14 which can slide in a bushing 15 integral to casing 7 and to first support 11. With nut screw element 14 engages a screw threaded shaft 16 pivotally connected to first support 11 and brought into rotation by a motor 17 via a gearing 18. A tooth 19 integral to nut screw element 14 guides the latter when translating since it engages with a groove 11a provided for in first support 11.

First support 11 is integral to housing 6 by means of a rigid plate 20. More precisely, plate 20 carries motor 9 and mechanically connects first support 11 and housing 6 through gearing 8. Shaft 5 of head 2 does not drive any axial forces to housing 6 even if pivotally connected with the latter, but it loads all the forces acting on drill bit 3 onto plate 20 via a flexion detector 21 and a pin 22, parallel and eccentric to shaft 5. Flexion detector 21 comprises strain gauges which correlate the flexion caused by the axial force of shaft 5 with the force itself, due to the resistance which the drill bit 3 meets in the body 4 while penetrating.

Figure 4A:
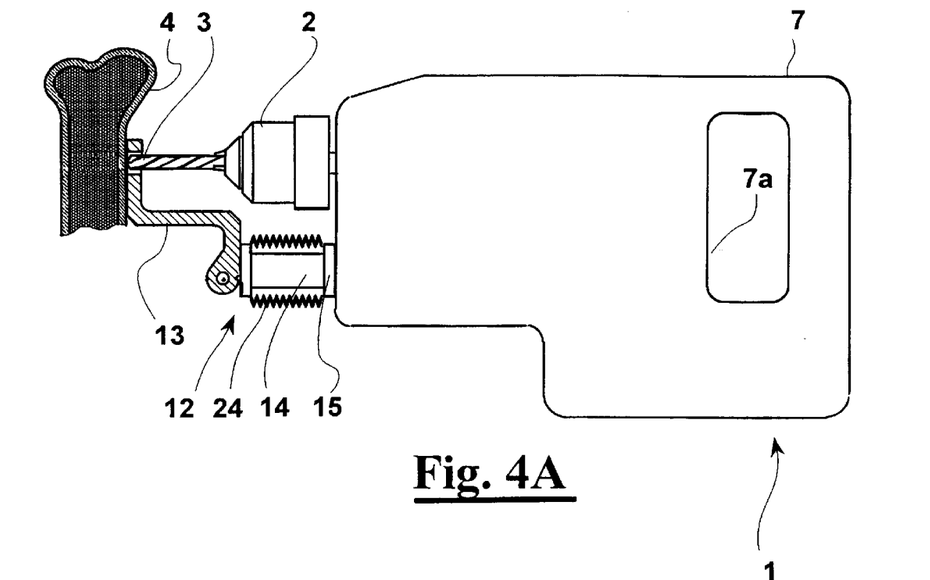
FIGS. 4A and 4B show an elevational lateral view of the drill of FIGS. 1 and 2 in two operative positions.
Figure 4B:
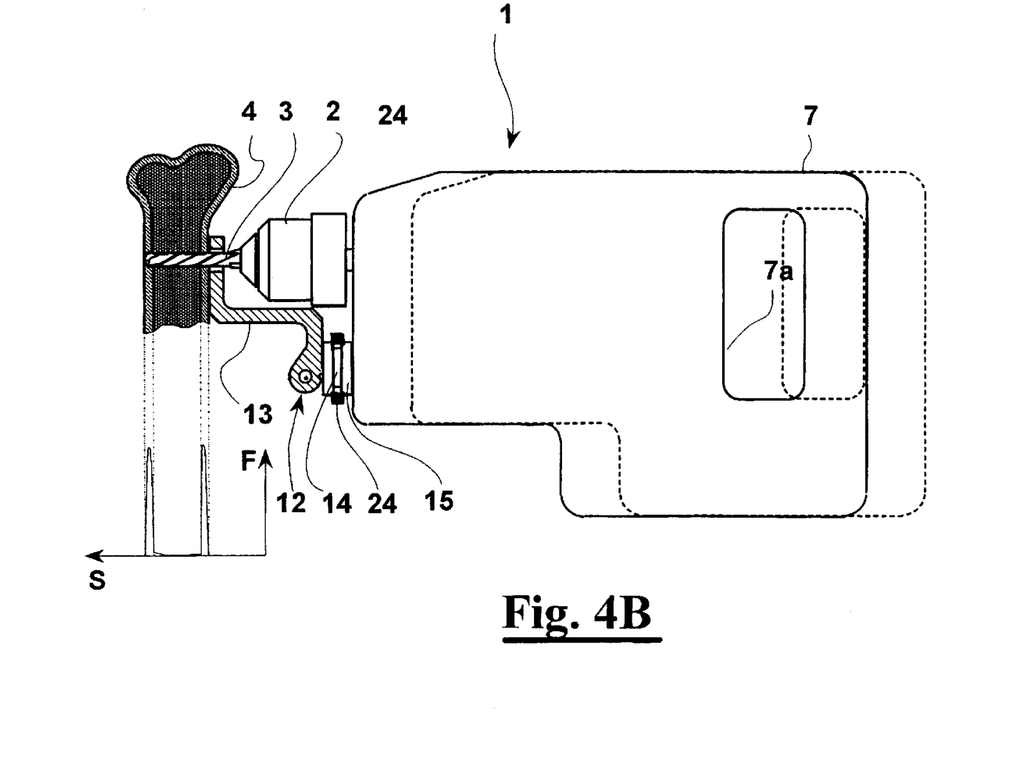

As shown in FIGS. 4A and 4B, the drilling step, that is the penetration of the rotating drill bit 3 through the body 4, is possible only when a relative movement between rest element 13 and drill bit 3 is carried out. More precisely, the surgeon, by means of actuating means, such as pedal means 23 (FIG. 1), starts the drill bit displacement with respect to second support 12 after having put the rest element 13 thereof over and then onto the exact point of the body 4 to bore. Drill bit 3, before that the drilling step starts, is arranged so that it does not protrude from rest element 13 outer surface, as shown in FIG. 4A and in FIG. 1 with dotted line.

As shown in FIG. 4B, like in many traditional drills, the holdable casing 7 of drill 1 moves with respect to the body to bore. However, according to the invention, drill bit displacement is not caused any more by the pushing force acting on the drill, but is caused by a relative movement of the first support with respect to the second support, which rests upon the body itself. The pushing force of the surgeon is only necessary to assure that rest element 13 is always kept in still contact with body 4.

The displacement of second support 12 with respect to first support 11 is caused by the rotation in nut screw element 14 of screw threaded bar 16, which is driven by motor 17 through gearing 18. Drill bit 3 displacement is advantageously controlled by an electronic unit not shown which analyses signals proportional to the force acting on drill bit 3 and discharged onto first support 11 through shaft 5, as detected by flexion sensor 21, or, equivalently, by a load cell of different kind. The measurement of the force in correlation with the drill bit displacement, according to a programmable logic residing in the electronic unit, operates the automatic block of the drill in certain critical conditions, such as the breakthrough detection of a cortical bone wall, or the drill bit reaching the second cortical bone wall after having crossed the trabecular bone, as shown in FIG. 2 or in FIG. 4B.

Always as shown in FIG. 2, the rest element 13 can be pivoted with respect to second support 12 about a pin 13a and put in a position of minimum encumbrance, shown with a dotted line, with the result that drill 1 could be used as a common surgical drill, that is with displacement controlled only by the push of the surgeon, depending on the preference of the latter choosing between an use according to the invention or a traditional use. Moreover rest element 13 could be pivoted in minimum encumbrance position when the drill is not used, so that the sensor and the mechanisms of the two supports are not damaged.

Obviously, in a simplified embodiment of drill 1, rest element 13 could be integral to second support 12, without possibility of being pivoted.

Holdable casing 7 according to the invention is preferably sealed, and it may comprise sealing means at the head 2 coupling with nut screw element 14. The latter, which variably protrudes from drill 1, may have a bellows 24, as shown in FIGS. 4A and 4B, which protects it from dirty and simplifies cleaning. In particular, the whole drill 1 could be sterilised by autoclave like whichever surgical tool.

Figure 5:
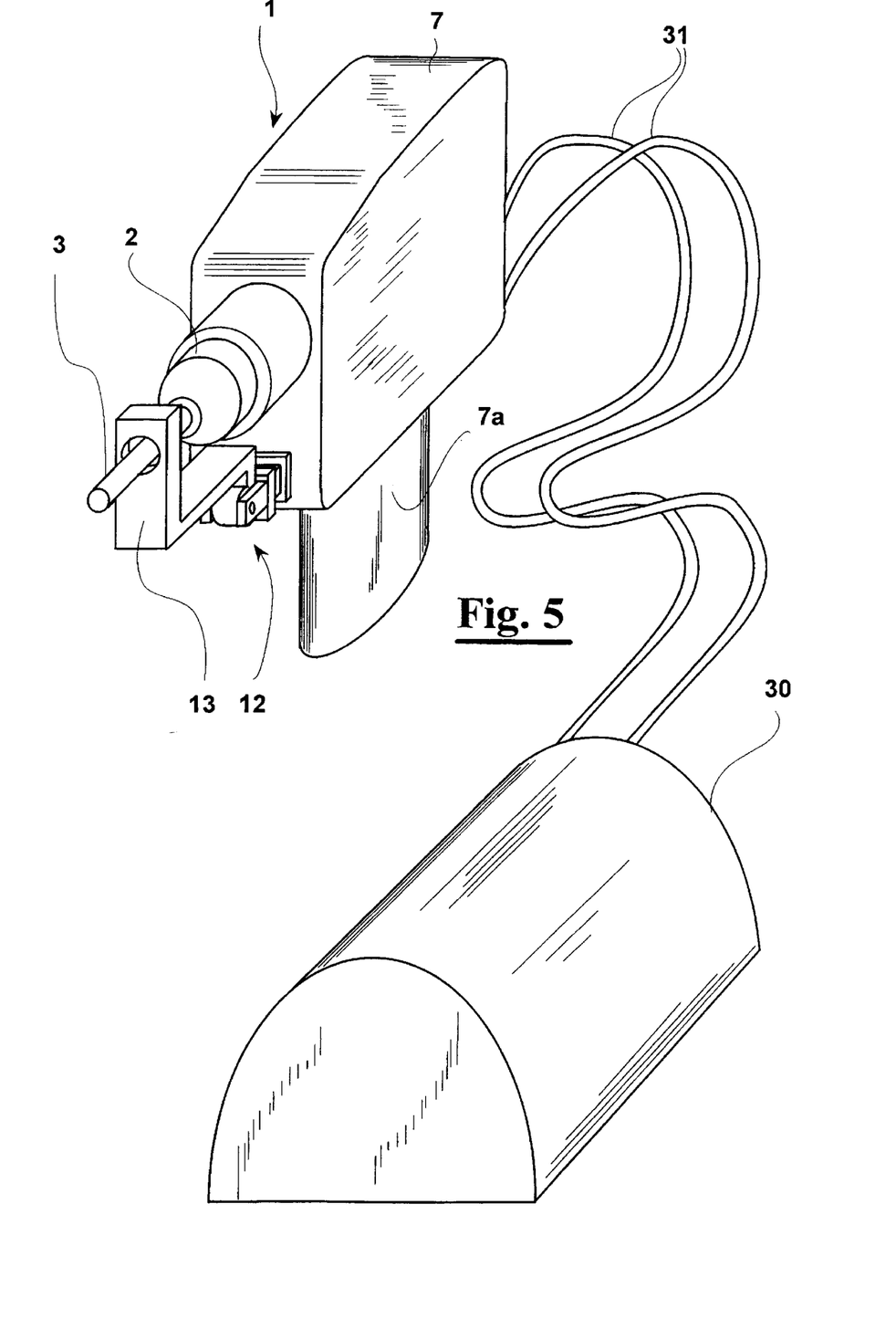
FIG. 5 shows a perspective view of a first different embodiment of the surgical drill of FIG. 1.

With reference to FIG. 5, a first different embodiment of drill 1 has a casing 7 of reduced encumbrance with respect to that of FIG. 1, thanks to a separated driving unit 30 and a protruding handgrip 7a. More precisely, driving unit 30 comprises internally the same motors 9 and 17 of head 2 and of actuating unit 10 respectively. The drive transmission is carried out by means of cables 31, and is of known type in the field of the medical apparatus, such as like that used for dentistry drills, and therefore is non described further.

Figure 6:
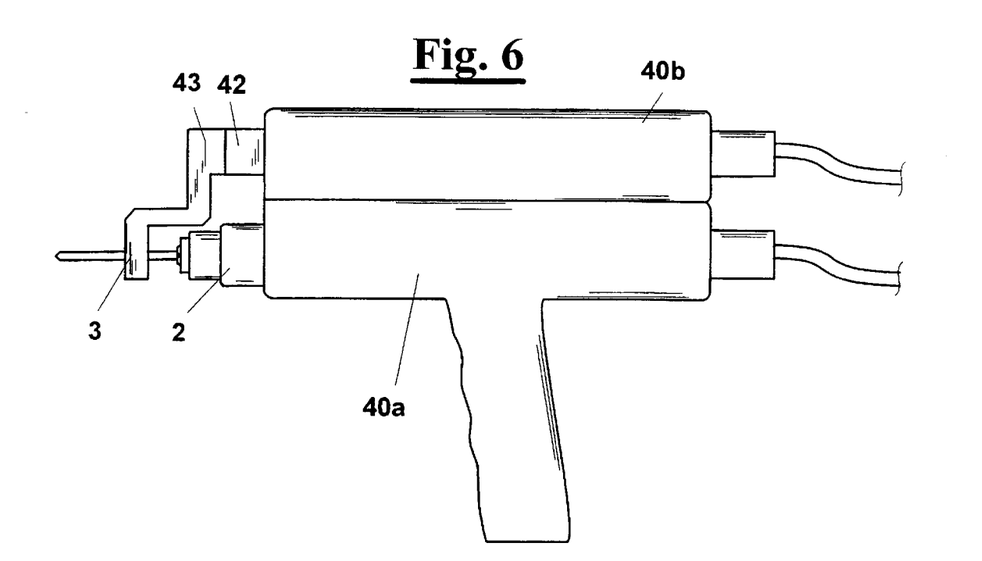
FIG. 6 shows a perspective view of a second different embodiment of the surgical drill of FIG. 1.

In a second different embodiment of the invention (FIG. 6) a drill 40a can be separated from its actuating unit 40b. In this case, drill 40a can be used as a normal drill when separated, as well as it can be used according to the invention when associated to actuating unit 40b in the manner described above. Drill 40a has inside the load cells for detecting the force, whereas actuating unit 40b controls the displacement of rest element 43 and second support 42 with respect to first support, which is provided for inside its casing.

Figure 7:
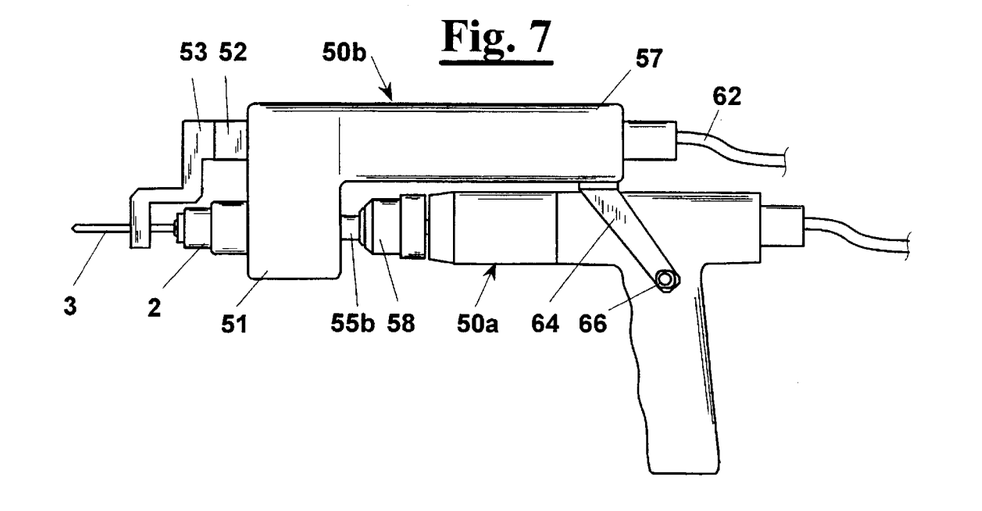
FIG. 7 shows a perspective view of a third different embodiment of the surgical drill of FIG. 1.
Figure 8:
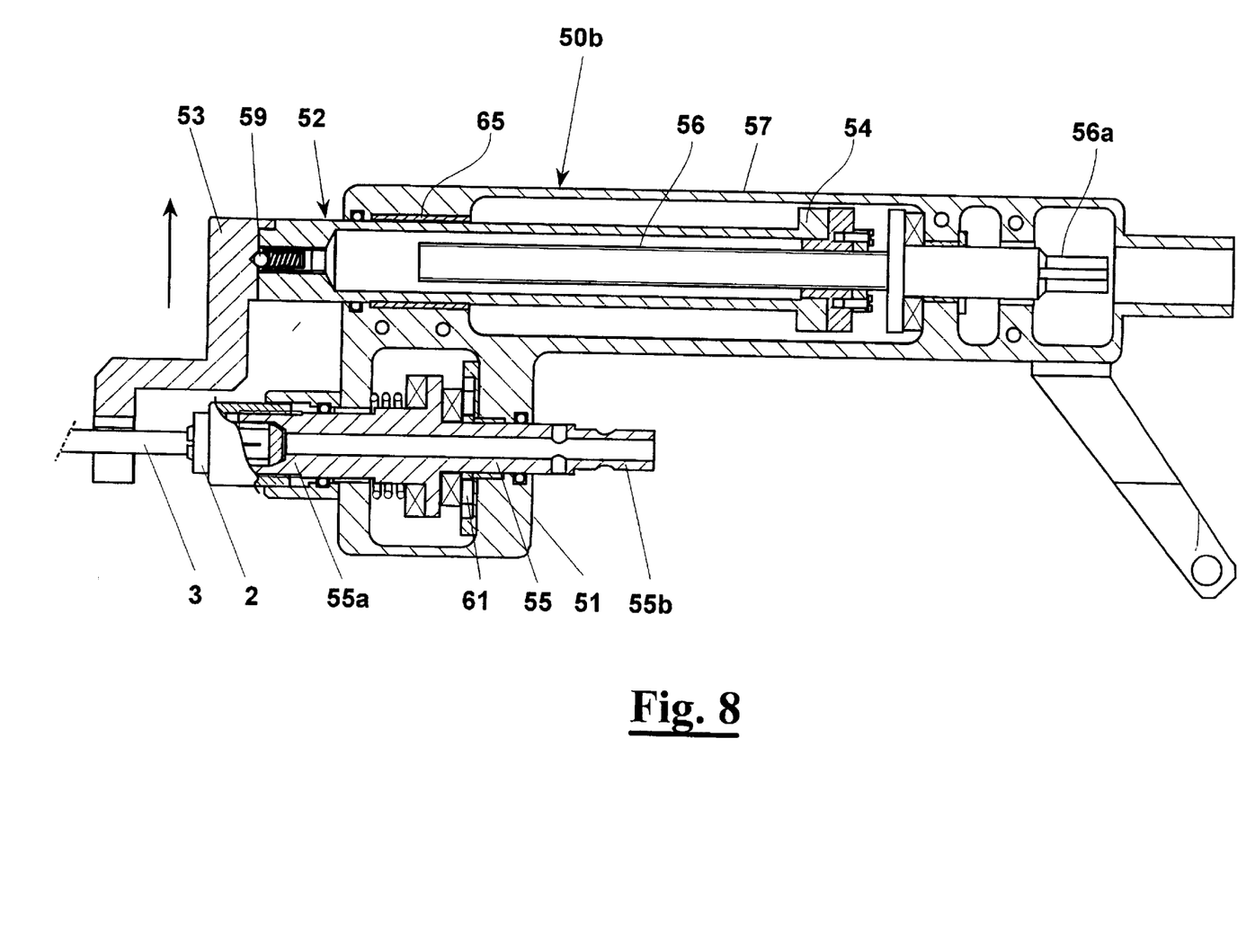
FIG. 8 shows a cross sectional view of an actuating unit of the embodiment of FIG. 7.

In a further embodiment of the invention, an actuating unit 50b (FIG. 7) is designed to be associated to a commercial surgical drill 50a which has not force sensors like drill 40a has. With reference also to FIG. 8, actuating unit 50b has a casing 57 with a first support 51 for a shaft 55 to which a drill bit 3 can be connected at its end 55a which supports head 2. Shaft 55 has the other end 55b capable of being gripped by a chuck head 58 of drill 50a (as shown in FIG. 7) and comprises a load cell disc 61 detecting axial forces transmitted by drill bit 3 during the drilling step. Pivotally connected to casing 57 a screw threaded bar 56 is provided for, engaging with a nut screw element 54 of a second support 52 having a rest element 53 at one end. Rest element 53 engages with nut screw element 54 by means of a dove tailed coupling (not visible in cross section) and a spring loaded ball 59, and can be disengaged in the direction of the arrow. Second support 52 is slidingly coupled to casing 57 by means of a bushing 65. End 56a of threaded bar 56 can engage with a transmission cable 62 (FIG. 1) connected to a driving unit not shown. Commercial drill 50a can be fastened to actuating unit 50b by coupling chuck 58 with end 55b and, at the same time, connecting brackets 64 to the drill by means of screws 66.

The embodiment of FIGS. 7 and 8 is particularly advantageous, since it allows the use of a normal surgical drill, reducing the cost of the whole apparatus when such drill is already available. In addition, according to the invention, it has the same advantages of the other embodiments already described above.

Both in the embodiment of FIGS. 1–3 and in the embodiments of FIGS. 5 to 8 the logic used to correlate force and displacement is preferably a "fuzzy" logic, already known and implemented in various robot apparatus. Using this logic, or other known mathematical methods, it is possible to obtain an algorithm which describes the reaction to penetration of drill bit 3 in body 4, as a function of the force detected and to the drill bit displacement, and it is thus possible to control precisely the drilling phase. In particular, in the case of a bone body having two cortical bone walls like that shown in FIG. 2, the control of the penetration of the drill bit in the body can be carried out with precision, with the possibility of blocking the drill bit displacement in the following critical cases:

at the breakthrough detection of the first cortical bone wall;

before beginning drilling the second cortical bone wall;

at the breakthrough detection of the second cortical bone wall.

As shown in the diagrams of FIGS. 2 and 4B, In fact, the force F detected by sensor 21 is at the maximum when crossing the cortical bone walls of a bone like body 4. Drill bit displacement S, which is equal to the actual drill bit displacement and opposite to the stroke of second support 12 with respect to first support 11, could be blocked automatically in the points of maximum variation of F with respect to S.

The drill and the actuating unit thereof according to the invention succeed in achieving the above objects. In particular, even if a fixed support for the drill cannot be provided for, it is possible, by resting directly against the body to bore, to control directly the progress of the drill bit when penetrating the tissues, as well as to control with precision the drill bit displacement and the drilling force limiting them in occasion of critical points. This is possible thanks to the presence of the second support, which has the function both of rest and of reference for the drill.

I claim:

1. A surgical drill, comprising a rotating head (2), in which a drill bit (3) suitable to bore a body (4) is mounted, and support means (7), to which said rotating head is pivotally connected, said support means comprising a first support (8) in which said rotating head (2) is housed and an actuating unit (10) of the displacement of said drill bit with respect to said body, characterised in that it comprises means (11,13, 16,17,21,22) for preventing a wall of said body from being broken through by said drill bit, said means for preventing comprising in combination:

a second support (13), suitable for resting directly upon said body and translating with respect to said first support (8) parallelly to said drill bit (3),     means for detecting (21,22) in said first support the force acting on said drill bit while drilling and     means for controlling (11,17)the displacement of said first support with respect to said second support and responsive to said means for detecting (21,22) of said force, whereby both a reliable guide of the drill bit and an automatic stop of the displacement of the drill bit in case of breakthrough condition are provided.

2. A surgical drill according to claim 1, wherein said means of detection of the force acting on said drill bit while drilling comprise at least a flexion detector (21, 22) which loads the axial force of said head on said first support.

3. A surgical drill according to claim 1, wherein said means of detection of the force acting on said drill bit while drilling comprise at least a load cell (61) provided for in said first support.

4. A surgical drill according to claim 1, wherein first screw means (16, 56) are provided for pivotally connected to said first support which engage with second screw means (14, 54) provided for on said second support, as well as means of transmission (56a,18) of the rotation of motor means to said first or second screw means.

5. A surgical drill according to claim 1, wherein said second support comprises a rest element (13) suitable for resting upon said body, said rest element being pivotally connected to said second support between an operative position and a position of minimum encumbrance.

6. A surgical drill according to claim 1, wherein said second support comprises a rest element (53) capable of resting upon said body, said rest element being releasably mounted on said second support.

7. A surgical drill according to claim 1, wherein said second support translates with respect to said first support and variably protrudes with respect to a bushing (15), sealing means (24) between said second support and said bushing being provided for comprising a bellows.

8. An actuating unit for a surgical drill (50a), comprising a rotating head (2) to which a drill bit (3) can be mounted and support means to which said rotating head is pivotally connected, said support means comprising a first support (51) in which said rotating head is housed, characterised in that it comprises means for preventing a wall of a body from being broken through by said drill bit, said rotating head being driven by said surgical drill (50a), said means for preventing comprising in combination:

a second support (53), suitable for resting directly upon said body and translating with respect to said first support parallelly to said drill bit,     means for detecting (61) in said first support the force acting on said drill bit (3) while drilling and     means for controlling (56) the displacement of said first support with respect to said second support and responsive to said means for detecting of said force, whereby both a reliable guide of the drill bit and an automatic stop of the displacement of the drill bit in case of breakthrough condition are provided.

9. An actuating unit according to claim 8, wherein said means of detection of the force acting on said drill bit while drilling comprise at least a flexion detector (21, 22) which loads the axial force of said head on said first support.

10. An actuating unit according to claim 8, wherein said means of detection of the force acting on said drill bit while drilling comprise at least a load cell (61) provided for in said first support.

11. An actuating unit according to claim 8 wherein said drill comprises a chuck (58) whereas said first support comprises a rotating shaft (55) integral at one end (55a) with said head (2) and has the other end (55b) suitable for being grasped by said chuck, said support means comprising a bracket releasably engageable with said drill, whereby said actuating unit can be used for the also with already existing surgical drills for steady guiding the drill bit and for stopping the displacement of the drill bit in case of breakthrough condition.

12. An actuating unit according to claim 8, wherein first screw means (16, 56) are provided for pivotally connected to said first support which engage with second screw means (14, 54) provided for on said second support, as well as means of transmission (56a,18) of the rotation of motor means to said first or second screw means.

13. An actuating unit according to claim 8, wherein said second support comprises a rest element (13) suitable for resting upon said body, said rest element being pivotally connected to said second support between an operative position and a position of minimum encumbrance.

14. An actuating unit according to claim 8, wherein said second support comprises a rest element (53) capable of resting upon said body, said rest element being releasably mounted on said second support.

15. An actuating unit according to claim 8, wherein said second support translates with respect to said first support and variably protrudes with respect to a bushing (15), sealing means (24) between said second support and said bushing being provided for comprising a bellows.

* * * * *